US005490831A

United States Patent [19]
Myers et al.

[11] Patent Number: 5,490,831
[45] Date of Patent: Feb. 13, 1996

[54] SELECTIVELY LOCKABLE KNEE BRACE

[75] Inventors: W. Neill Myers; Michael D. Shadoan; John C. Forbes, all of Huntsville; Kevin J. Baker, Cullman; Darron C. Rice, Albertville, all of Ala.

[73] Assignee: The United States of America as represented by the Administrator, National Aeronautics and Space Administration, Washington, D.C.

[21] Appl. No.: 252,032

[22] Filed: May 25, 1994

[51] Int. Cl.⁶ ................................................ A61F 5/00
[52] U.S. Cl. .............................. 602/26; 602/16; 623/44
[58] Field of Search ................................... 602/5, 16, 23, 602/26; 623/39–44

[56] References Cited

U.S. PATENT DOCUMENTS

| | | | |
|---|---|---|---|
| 2,512,826 | 6/1950 | Clark | 602/26 |
| 2,522,853 | 9/1950 | Black | 602/23 X |
| 2,594,227 | 4/1952 | Smith | 623/44 |
| 2,646,793 | 7/1953 | Swiech et al. | 623/44 X |
| 2,943,622 | 7/1960 | Nelson | 623/44 X |
| 3,408,660 | 11/1968 | Walters | 623/44 X |
| 4,179,759 | 12/1979 | Smith | 623/44 X |
| 4,456,003 | 6/1984 | Allard et al. | 623/44 X |
| 4,688,559 | 8/1987 | Vito et al. | 623/43 X |

*Primary Examiner*—Linda C. Dvorak
*Attorney, Agent, or Firm*—Robert L. Broad, Jr.

[57] ABSTRACT

A knee brace for aiding in rehabilitation of damaged leg muscles includes upper and lower housings normally pivotable one relative to the other about the knee joint axis of a patient. The upper housing is attachable to the thigh of the patient above the knee joint while the lower housing is secured to a stirrup which extends downwardly along the patient's leg and is attached to the patient's shoe. An actuation rod is carried within the lower housing and is coupled to a cable. The upper and lower housings carry cooperative clutch/brake elements which normally are disengaged to permit relative movement between the upper and lower housings. When the cable is extended the clutch/brake elements engage and lock the housings together. A heel strike mechanism fastened to the stirrup and the heel of the shoe is connected to the cable to selectively extend the cable and lock the brace in substantially any position when the patient places weight on the heel.

26 Claims, 2 Drawing Sheets

SELECTIVELY LOCKABLE KNEE BRACE

ORIGIN OF THE INVENTION

This invention was made by employees of the United States Government and may be manufactured and used by or for the Government for governmental purposes without the payment of any royalties.

BACKGROUND OF THE INVENTION

1. Field of the Invention

This invention relates to a knee brace and more particularly to a knee brace that when worn by a person permits the knee to become rigid in substantially any position of the leg and to become flexible so as to bend, the brace being actuated to lock in substantially any leg position or being deactivated to unlock and pivot as controlled through an actuation device selectively by the user.

2. Description of Related Art

It is known to utilize a knee brace in the rehabilitation of persons who have suffered muscle damage in a leg, such as that as may occur as a result of an injury or a paralysis resulting from a stroke or the like. The construction of prior art knee braces are such that they lock the knee into a rigid straight leg position only. A manual release in the form of a pull pin is provided which must be pulled by the user in order to unlock the brace so that the leg may bend. The knee joint may move until the pin is manually reinserted. This limits or precludes flexibility of the knee and thus rehabilitation of the knee muscles. Additionally, not only is a manual unlocking of the brace required when it is desired to bend the knee, but the brace will only support a load in the locked straight leg position. Thus, the user may only walk stiff-legged with the brace in the locked straight leg position.

SUMMARY OF THE INVENTION

Consequently, it is a primary object of the present invention to provide a rehabilitative knee brace, the brace permitting movement of the knee joint of the user and being selectively locked into substantially any position.

It is another object of the present invention to provide a knee brace which normally permits pivotal movement of the knee of a person rehabilitating from muscle damage in a leg and which may lock into substantially any position by readily activating locking means selectively controlled by the user.

It is a further object of the present invention to provide a knee brace which normally permits pivotal movement of a knee of a person rehabilitating from muscle damage in a leg and which may be locked into substantially any position by the user engaging a heel strike mechanism against the floor to activate locking means in the brace.

Accordingly, the present invention provides a knee brace that includes first and second housing members normally pivotable one relative to the other about the knee joint axis of a user of the brace, one of the housings being attachable to a thigh harness above the knee joint and the other housing being secured to a stirrup or the like which extends downwardly along the leg of the user below the knee joint and attached to means fixed to the lower portion of the leg, such means preferably being an actuation mechanism secured to a shoe of the user. An actuation rod is carried within the lower of the two housings and is coupled to an actuation cable. The two housings carry respective cooperative surface elements of a clutch/brake that normally permits movement of the housings relative to one another, but when the actuation cable is extended the surfaces of the clutch/brake elements are forced to engage and thereby lock the brace. Extension of the cable may occur at any position of the lower housing relative to the upper housing so that the brace and thus the knee may be locked in any position. A control device may be connected to the actuation cable and selectively engaged to extend the cable to lock the brace. Preferably, such control device comprises a heel strike mechanism fastened to the stirrup and the heel of the shoe of the person using the brace and when the user places weight on the heel, the cable will extend. The heel strike mechanism may comprise lever means connected to a strike member to effect extension of the actuation cable when the user applies weight to the strike member.

BRIEF DESCRIPTION OF THE DRAWINGS

The particular features and advantages of the invention as well as other objects will become apparent from the following description taken in connection with the accompanying drawings in which.

DESCRIPTION OF THE PREFERRED EMBODIMENTS

Figure 1:
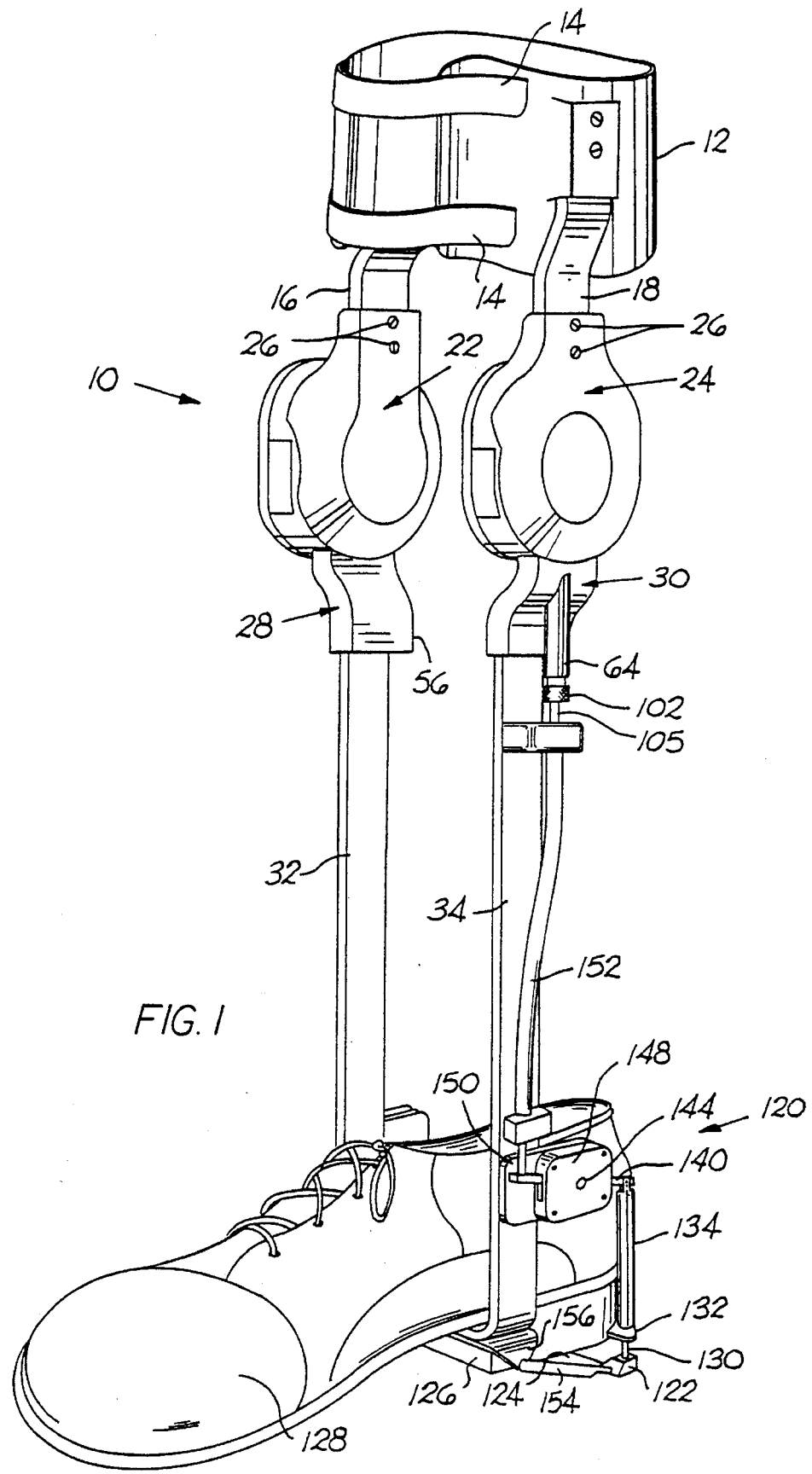
FIG. 1 is a perspective view of a lockable knee brace constructed in accordance with the present invention and connected to a heel strike mechanism attached to a shoe of a person wearing the brace.

Referring now to the drawings, a knee brace 10 constructed in accordance with the present invention includes a form fitting restraint or harness 12 for attachment to the patient above the knee by, for example, encircling the thigh of the patient. The harness includes straps 14 which may be secured at one end to the harness and connected by fastener means such as hook and loop fasteners sold under the trade name VELCRO at its other ends. Secured within pockets to the harness at each side thereof so as to be disposed along the outer and inner sides of the leg of a patient is a respective outer and inner upper stirrup 16, 18. The lower end of each stirrup is received within a seat 20 in the upper end of a respective upper housing 22, 24 and is secured therein by fasteners such as screws 26.

The physiology of the knee brace 10 requires that each side thereof be different in orientation but each includes identical mechanisms including a respective outer and inner lower housing 28, 30 and stirrups 32, 34 fastened to the respective bottom ends of the lower housings by fastener means such as screws 36. Since the internal mechanism is identical, only that associated with the outer side of the brace, i.e., the left side in FIG. 1, will be described.

Each upper housing, such as housing 22, is closed at one side and, except as hereinafter described, open at the other side. Disposed within and opening onto the open side is an internal cavity having a central well 38 substantially concentric about the axis 40 of the knee joint when the brace is being worn. An annular recess or annulus 42 is spaced from and substantially concentric about the central well 38 and thus the axis 40. The radially inner wall 44 of the annular recess 42 has a substantially cylindrical configuration while the radially outer wall 46 is tapered so that it has a substantially truncated conical configuration. Positioned about the inner wall 44 is the inner race of a needle bearing 48, the outer race being secured to the inner surface of an annular hub 50 projecting outwardly from one side of the corresponding lower housing 28 and into the open side and cavity of the upper housing. The outer surface 52 of the hub 50 has substantially the same conical configuration as that of the outer wall 46 of the recess 42 of the upper housing so that the conical surfaces 46 and 52 may mate. Each surface 46, 52 has a viton rubber layer vulcanized thereon so as to form the mating surfaces of a conical clutch/brake. When the clutch/brake surfaces 46, 52 are disengaged, the lower housing may pivot relative to the upper housing as the hub 50 rotates and pivots on the needle bearings, but when the surfaces 46 and 52 are engaged, the lower housing is locked to the upper housing.

The lower housing 28 is an elongated member having an axially elongated passageway 54 extending vertically when the brace is worn, the passageway 54 being substantially cylindrical in form and extending from the upper end of the housing 28 to open adjacent the lower end. The lower end 56 of the lower housing 28 is offset relative to the axis of the passageway 54 toward the other side of the brace, i.e., toward the side having the housings 24 and 30, and the stirrup 32 is connected to the bottom thereof as aforesaid. The stirrup 32 is thus disposed adjacent the leg of the user with the passageway 54 further remote from the leg. Preferably the upper end of the passageway 54 has an opening 58 for reasons hereinafter described. Additionally, in the central portion of the annular hub 50 the lower housing includes a tab 60 which projects into the well 38 of the upper housing for reasons hereinafter made clear.

Figure 2:
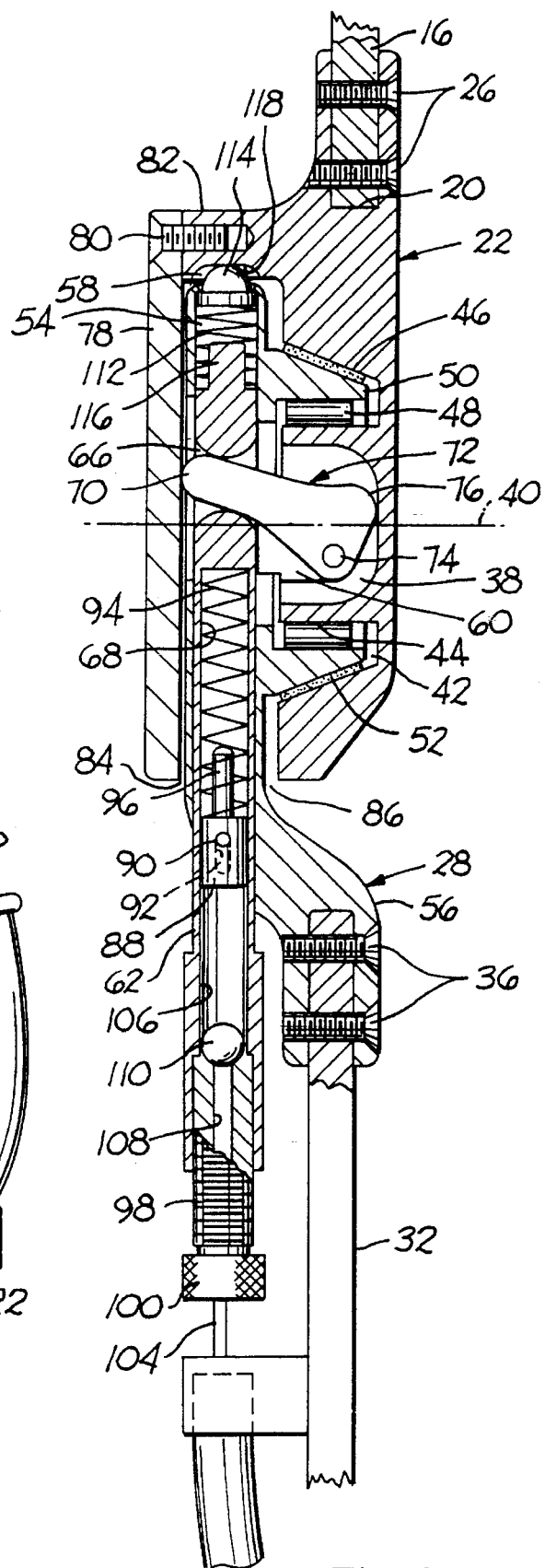
FIG. 2 is a cross sectional view taken substantially along the longitudinal plane through the brace elements at one side of the brace illustrated in FIG. 1.

Positioned within the passageway 54 of the lower housing is an elongated actuation rod 62, the rod 62 extending out the opening in the housing adjacent the offset lower end 56. A similar actuation rod 64 is, of course, associated with the lower housing 30 as illustrated in FIG. 1. The actuation rod 62 is an elongated cylindrical member having a substantially solid upper portion below the top of which a through opening or slot 66 is formed. Below the slot 66 in the lower portion of the rod 56 is an axially elongated bore 68 which opens at the lower end of the rod. Positioned within and extending through the slot 66 is a projecting finger or lever portion 70 of a cam 72 pivotally mounted on a pin 74 secured to the tab 60 of the lower housing. The width of the finger in the vertical direction as illustrated in FIG. 2 is slightly less than the width of the slot 66 in the vertical direction so that it may be moved when the actuation rod 62 is moved. Moreover, the finger or lever portion 70 of the cam 72 is disposed in abutment with the interior wall of the back-plate 78.

The cam 72 also includes a bull-nose lobe 76 which may abut the wall of the well 38 of the upper housing remote from the open side of the housing selectively. A back-plate 78 is secured as by screws 80 to a laterally extending portion 82 of the upper housing preferably formed about substantially the entire open side of the upper housing except at the bottom where the offset portion of the lower housing protrudes and a small rear portion adjacent the two housings, the back-plate thus effectively forming a part of the upper housing. A clearance 84 is thus formed between the plate 78, and thus the upper housing, and the lower housing 28, and a similar clearance 86 is formed between the lower housing 28 and the bottom portion of the upper housing. These clearances permit the lower housing to pivot from the disposition where the lower end 56 of the lower housing 28 and the stirrup 32 are vertical to a disposition where the lower end 56 and the stirrup 32 are disposed rearwardly and at an angle to the vertical, this latter disposition being that of the leg of the user when the knee is bent as during walking.

Thus, when the actuation rod 62 is moved within the passageway 54 the finger or lever portion 70 of the cam 72 is driven by the actuation rod to pivot the cam 72 about the pin 74. When the rod 62 is moved upwardly in the passageway, the cam 72 is pivoted clockwise as illustrated in FIG. 2, and in the opposite direction or counter-clockwise when the rod is moved downwardly. Rotation of the cam 72 in the clockwise direction as illustrated results in the lobe 76 abutting and acting against the upper housing to force the upper housing 22 away from the lower housing 28 and the clutch surfaces 46, 52 to be disengaged, as is the position illustrated in FIG. 2. However, when the cam 72 is rotated counter-clockwise the free end of the finger 70 acts against the back-plate 78 to force the clutch surfaces 46, 52 to engage, the lobe 72 in this latter condition being rotated to a disposition where it is not forced against the wall of the upper housing.

Positioned within the bore 68 of the actuation rod 62 substantially intermediate its length is a plug 88 which carries a pin 90, the pin 90 extending through a slot 92 in the actuation rod 62. A coil spring 94 is disposed within the bore 68 of the actuation rod 62, the lower end of the spring being positioned about a nub 96 on the upper end of the plug 88 while the lower end of the spring 94 abuts a seat formed by bottom of the solid portion of the actuation rod at the top of the bore 68. The spring 94 acts as a return spring for the actuation rod while the pin 90 and slot 92 act to limit the travel of the actuation rod. Thus, when the rod is pulled downwardly, the pin 90 engages the upper edge of the slot 92 and the spring 94 is compressed. When the downward pull on the rod is released, the spring 94 returns the actuation rod to its upper position.

Threadedly connected within the lower end of the bore 68 of the actuation rod 62 is a threaded rod 98 preferably having a knurled head 100 at its external end. A similar screw having a knurled head 102 is, of course, associated with the actuation rod 64 at the other side of the brace as illustrated in FIG. 1. A pull cable 104 is coupled to the threaded rod so as to translate therewith within the actuation rod but the cable is not rotatable with the threaded rod. To this end the threaded rod 98 may have a hollow interior 106 at its upper end and a narrow bore 108 extending through the head 100 and the threaded rod 98 to open into the hollow 106, while a ball 110 at the upper end of the cable couples the cable to the threaded adjustment rod 98. Thus, rotation of the knurled head may effect adjustment of the tension of the cable 104 without twisting the cable.

An optional detent for providing a slight retaining force on the actuation rod 62 and thus the cam 72 when the apparatus is in the locked or straight leg position may be included by means of a preloaded coil spring 112 disposed between the top of the actuation rod and a detent ball 114. The spring may be disposed at its lower end about a nub 116 on top of the actuation rod 62 while the ball 114 abuts the top of the spring and is forced partly through the opening 58 by the spring against an arcuate seat or recess 118 formed on the upper housing 22.

Figure 3:
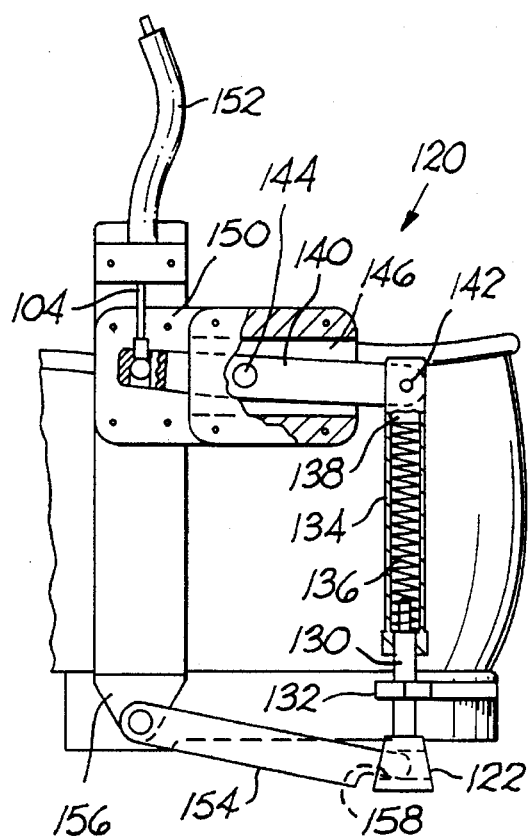
FIG. 3 is an elevational view partly in cross section of the heel strike mechanism illustrated in FIG. 1.

Control of the pull cable 104 may be provided by means actuated by the user. The preferred means for this control is a heel strike mechanism 120 such as illustrated in FIGS. 1 and 3. This device includes a strike bar 122 having a lateral portion 124 extending beneath the heel 126 of the shoe 128 of the wearer. Fastened to the strike bar 122 are two assemblies, one at each side of the heel 126 for activating the two clutch/brakes in the knee brace, i.e., the clutch/brakes at each side of the brace. Since each of these assemblies are identical, only one of the mechanisms is fully disclosed and described herein.

Each heel strike mechanism assembly includes push rod means which comprises a plunger 130 fastened to the strike bar 122 or to the laterally extending portion 124 of the strike bar, the plunger being journally supported by a plate 132 fixed to the shoe heel, there of course being one at each side of the heel. The plunger 130 extends within a cylindrical tube 134 within which a preloaded coil spring 136 is disposed, the bottom of the spring abutting a ledge or the like at the upper end of the plunger while the top of the spring abuts a plug or cap 138 adjacent the top of the tube. The top of the tube has a bifurcated portion, best illustrated in FIG. 1, within which one end of a lever 140 is disposed and journally carried on a pin 142. The lever 140 is hinged about a pivot pin 144 disposed within a pivot block 146 protected by a cover 148 and secured to a plate 150, the lever extending from both ends of the pivot block. The plate 150 and thus the pivot block 146 is secured to the respective stirrup such as stirrup 34 of the leg brace and the lower end of the respective cable 104, 105 is fastened to the end of the lever 140 remote from the end fastened to the tube, i.e., remote from the pin 142. The stirrups 32 and 34 are bent at the bottom ends and attached to the shoe 128. Preferably, a sheath 152 protects the cable. Additionally, a scuff plate 154 may be mounted beneath the heel of the shoe pivoted on a bracket 156 at one end and having its other end engaging a slot 158 in the strike bar 122 to protect it from catching on irregular surfaces.

In operation, the patient or wearer of the brace may initiate an input force when the strike bar 122 makes contact with the floor or ground and weight is applied. The amount of force is regulated by the overload spring 136 within the tube 134 and may be fined tuned for each patient. The cables at each side of the brace transfer the actuation force to the two sides of knee brace. Thus, when it is desired to lock the upper and lower housings and thus the knee joint, the strike bar is engaged against the floor. This forces the plunger 130 and tube 134 upwardly to pivot the lever 140 about the pin 144 in a counter-clockwise direction as illustrated in FIG. 3. The cables 104, 105 are thus pulled downwardly pulling the respective actuating rod 62 down relative to the respective lower housing 28, 30. This compresses the return spring 94 and causes the cam 72 to rotate counter-clockwise as illustrated in FIG. 2 about the pin 74. Rotation of the cam 72 causes the finger portion 70 of the cam to apply a force to the back-plate 78 thereby forcing the back-plate and each respective upper housing 22, 24 toward the respective lower housing 28, 30 resulting in engagement of the surfaces 46 and 52 of the clutch/brakes. This locks the brace members and thus the knee joint. When the heel strike bar 122 is disengaged from the ground, tension on the cables 104, 105 is released. The actuation rod returns to its upper position and the cam 72 rotates back toward the disposition illustrated in FIG. 2 where the lobe 76 abuts the respective upper housing forcing the upper housings away from the respective lower housings thereby resulting in disengagement of the clutch/brake surfaces 46, 52 and permitting the lower housings to move relative to the upper housings so that the knee joint may bend.

Accordingly, the present invention provides a knee brace which may be locked or unlocked selectively. Thus, a patient rehabilitating from muscle damage in his or her leg is permitted flexible knee movement, which aids the rehabilitation program. Moreover, it permits the patient to walk in a relatively normal manner without being stiff-legged.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. A knee brace for a patient rehabilitating from leg damage, said brace comprising harness means for attachment about the leg of the patient above the knee, articulating brace means positionable at each side of the knee, each articulating brace means having an upper housing and a lower housing, means for securing each upper housing at a respective side of the leg of the patient to said harness, an elongated stirrup secured to each lower housing and adapted to extend lengthwise along a respective side of the leg of the patient below the knee, means for securing each stirrup to the leg of the patient below the knee, journal means for pivotably mounting each lower housing relative to a respective upper housing for relative movement about a lateral axis positionable so as to be substantially aligned with the knee, each upper housing having first clutch surface means, each lower housing having second clutch surface means corresponding to and engageable selectively with the first clutch surface means of a corresponding upper housing for permitting movement of the lower housings relative to the respective upper housing when the first and second surface means are disengaged and for locking the lower housing to the respective upper housings when the first and second surface elements engage, an actuator carried by and movable relative to each lower housing, each actuator having an abutment means moveable in a first direction for forcing the respective upper housing laterally substantially along said axis in one direction for engaging said first and second clutch surface means and moveable in a second direction for forcing the respective upper housing laterally substantially along said axis in a direction opposite to said one direction for disengaging said first and second clutch surface means, and control means adapted to be operable by movement of the leg of the patient connected to each actuator for moving each respective abutment means in said first and second directions selectively to move said upper housings relative to said lower housings for engaging or disengaging said first and second surface means whereby said lower housings may be locked relative to said upper housings or may pivot relative thereto about said lateral axis.

2. A knee brace as recited in claim 1, wherein each upper housing includes an annular cavity substantially concentric about said axis, said cavity having an inner wall and an outer wall, said journal means being disposed about one of said inner and outer walls, said first clutch surface means being defined about the other of said inner and outer walls, each lower housing having an annular hub including an inner wall and an outer wall, one of said inner and outer walls of said hub being disposed about said journal means for rotation of said lower housing relative to said upper housing, and said second clutch surface means being disposed about the other of said inner and outer walls of said hub.

3. A knee brace as recited in claim 1, wherein each actuator includes an elongated member, means for slidably mounting each elongated member in a respective lower housing for movement relative to said upper and lower housings, means for mounting each abutment means for pivoting about an axis transverse to said lateral axis for movement in said first direction in response to a downward movement of said elongated member and for movement in said second direction in response to an upward movement of said elongated member.

4. A knee brace as recited in claim 1, wherein said control means includes a cable coupled to each actuator, lever means carried by each stirrup and operable to selectively apply tension to said cable to move said actuator and thereby said abutment means in said first direction and force said upper housing in said one direction.

5. A knee brace as recited in claim 2, wherein each actuator includes an elongated member, means for slidably mounting each elongated member in a respective lower housing for movement relative to said upper and lower housings, means for mounting each abutment means for movement in said first direction in response to a downward movement of said elongated member and for movement in said second direction in response to an upward movement of said elongated member.

6. A knee brace as recited in claim 2, wherein said control means includes a cable coupled to each actuator, lever means carried by each stirrup and operable to selectively apply tension to said cable to move said actuator and thereby said abutment means in said first direction and force said upper housing in said one direction.

7. A knee brace as recited in claim 3, wherein said control means comprises a cable coupled to each actuator, lever means carried by each stirrup and operable to selectively pull said cable to move said actuator and thereby said abutment means in said first direction and force said upper housing in said one direction.

8. A knee brace as recited in claim 1, wherein said means for securing each stirrup to the leg of the patient includes a shoe worn on the foot of the patient, means for securing each of said stirrups to said shoe, a depressible strike member mounted on said shoe and disposed for selectively engaging a floor beneath said shoe, means for connecting said strike member to said actuator for moving said abutment means in said first direction when said strike member is forced against said floor.

9. A knee brace as recited in claim 3, wherein each abutment means comprises a cam rotatably journalled in a respective lower housing, each said cam having a finger abutting said elongated member and moveable in response to movement of said elongated member to rotate said cam in said first and second directions selectively, said finger having a free end engageable with said upper housing when said cam is rotated in said first direction to force said upper housing in said one direction, said cam having a lobe engageable with said upper housing when said cam is rotated in said second direction to force said upper housing in said direction opposite to said one direction.

10. A knee brace as recited in claim 9, wherein said control means includes a cable coupled to each actuator, lever means carried by each stirrup and operable to selectively apply tension to said cable to move said actuator and thereby said abutment means in said first direction and force said upper housing in said one direction.

11. A knee brace as recited in claim 4, wherein said means for securing each stirrup to the leg of the patient includes a shoe worn on the foot of the patient, means for securing each of said stirrups to said shoe, a depressible strike member mounted on said shoe and disposed for selectively engaging a floor beneath said shoe, means for connecting said strike member to said actuator for moving said abutment means in said first direction when said strike member is forced against said floor.

12. A knee brace as recited in claim 2, wherein said journal means is disposed about said inner wall of said cavity and the inner wall of said hub.

13. A knee brace as recited in claim 5, wherein each abutment means comprises a cam rotatably journalled in a respective lower housing, each said cam having a finger abutting said elongated member and moveable in response to movement of said elongated member to rotate said cam in said first and second directions selectively, said finger having a free end engageable with said upper housing when said cam is rotated in said first direction to force said upper housing in said one direction, said cam having a lobe engageable with said upper housing when said cam is rotated in said second direction to force said upper housing in said direction opposite to said one direction.

14. A knee brace as recited in claim 9, wherein said control means comprises a cable coupled to each actuator, lever means carried by each stirrup and operable by the foot of the patient to selectively pull said cable to move said actuator and thereby said abutment means in said first direction and force said upper housing in said one direction.

15. A knee brace as recited in claim 2, wherein said means for securing each stirrup to the leg of the patient includes a shoe worn on the foot of the patient, means for securing each of said stirrups to said shoe, a depressible strike member mounted on said shoe and disposed for selectively engaging a floor beneath said shoe, means for connecting said strike member to said actuator for moving said abutment means in said first direction when said strike member is forced against said floor.

16. A knee brace as recited in claim 15, wherein said journal means is disposed about said inner wall of said cavity and the inner wall of said hub.

17. A knee brace as recited in claim 15, wherein each actuator includes an elongated member, means for slidably mounting each elongated member in a respective lower housing for movement relative to said upper and lower housings, means for mounting each abutment means for pivoting about an axis transverse to said lateral axis for movement in said first direction in response to a downward movement of said elongated member and for movement in said second direction in response to an upward movement of said elongated member.

18. A knee brace as recited in claim 8, wherein said control means comprises a cable coupled to each actuator, lever means carried by each stirrup and operable to selectively pull said cable to move said actuator and thereby said abutment means in said first direction and force said upper housing in said one direction.

19. A knee brace as recited in claim 18, wherein each actuator includes an elongated member, means for slidably mounting each elongated member in a respective lower housing for movement relative to said upper and lower housings, means for mounting each abutment means for movement in said first direction in response to a downward movement of said elongated member and for movement in said second direction in response to an upward movement of said elongated member.

20. A knee brace as recited in claim 19, wherein each abutment means comprises a cam rotatably journalled in a respective lower housing, each said cam having a finger abutting said elongated member and moveable in response to movement of said elongated member to rotate said cam in said first and second directions selectively, said finger having a free end engageable with said upper housing when said cam is rotated in said first direction to force said upper housing in said one direction, said cam having a lobe engageable with said upper housing when said cam is rotated in said second direction to force said upper housing in said direction opposite to said one direction.

21. A knee brace as recited in claim 13, wherein said means for securing each stirrup to the leg of the patient includes a shoe worn on the foot of the patient, means for securing each of said stirrups to said shoe, a depressible strike member mounted on said shoe and disposed for selectively engaging a floor beneath said shoe, means for connecting said strike member to said actuator for moving said abutment means in said first direction when said strike member is forced against said floor.

22. A knee brace as recited in claim 21, wherein said control means comprises a cable coupled to each actuator, lever means carried by each stirrup and operable to selectively pull said cable to move said actuator and thereby said abutment means in said first direction and force said upper housing in said one direction.

23. A knee brace as recited in claim 6, wherein said means for securing each stirrup to the leg of the patient includes a shoe worn on the foot of the patient, means for securing each of said stirrups to said shoe, a depressible strike member mounted on said shoe and disposed for selectively engaging a floor beneath said shoe, means for connecting said strike member to said actuator for moving said abutment means in said first direction when said strike member is forced against said floor.

24. A knee brace as recited in claim 6, wherein each abutment means comprises a cam rotatably journalled in a respective lower housing, each said cam having a finger abutting said elongated member and moveable in response to movement of said elongated member to rotate said cam in said first and second directions selectively, said finger having a free end engageable with said upper housing when said cam is rotated in said first direction to force said upper housing in said one direction, said cam having a lobe engageable with said upper housing when said cam is rotated in said second direction to force said upper housing in said direction opposite to said one direction.

25. A knee brace as recited in claim 5, wherein said journal means is disposed about said inner wall of said cavity and the inner wall of said hub.

26. A knee brace as recited in claim 6, wherein said journal means is disposed about said inner wall of said cavity and the inner wall of said hub.

* * * * *